United States Patent [19]
Yoshimatsu et al.

[11] Patent Number: 6,001,633
[45] Date of Patent: Dec. 14, 1999

[54] CELLS PRODUCING RECOMBINANT RETROVIRUS

[75] Inventors: Tadanori Yoshimatsu, Hiroshima; Kazuhiro Ikenaka, Aichi, both of Japan

[73] Assignee: Wakunaga Seiyaku Kabushiki Kaisha, Osaka, Japan

[21] Appl. No.: 08/952,671

[22] PCT Filed: May 31, 1996

[86] PCT No.: PCT/JP96/01484

§ 371 Date: Mar. 31, 1998

§ 102(e) Date: Mar. 31, 1998

[87] PCT Pub. No.: WO96/38545

PCT Pub. Date: Dec. 5, 1996

[30] Foreign Application Priority Data

Jun. 2, 1995 [JP] Japan ................................ 7-136877

[51] Int. Cl.[6] .............................. C12N 7/00; C12N 7/02; C12N 5/00
[52] U.S. Cl. .................. 435/235.1; 435/465; 435/467; 435/236; 435/239; 435/325; 435/352; 435/354
[58] Field of Search ....................... 435/440, 455, 435/456, 465, 466, 467, 235.1, 236, 239, 325, 352, 354

[56] References Cited

PUBLICATIONS

Korman et al., *Proc. Natl. Acad. Sci. USA* 84:2150–2154, Apr. 1987.

Yoshimatsu et al., *Hum. Gene Ther.* 9:161–172, Jan. 20, 1998.

*Primary Examiner*—Robert D. Budens
*Attorney, Agent, or Firm*—Oblon, Spivak McClelland, Maier & Neustadt, P.C.

[57] ABSTRACT

An objective of the present invention is to provide a packaging cell for preparing a retrovirus having a high viral titer. The cell producing a recombinant retrovirus is constructed by introducing, the Polyoma virus early region gene together with a recombinant plasmid or a recombinant retrovirus free from any replication origin derived from Polyoma virus into a packaging cell for preparing a recombinant retrovirus.

14 Claims, 2 Drawing Sheets

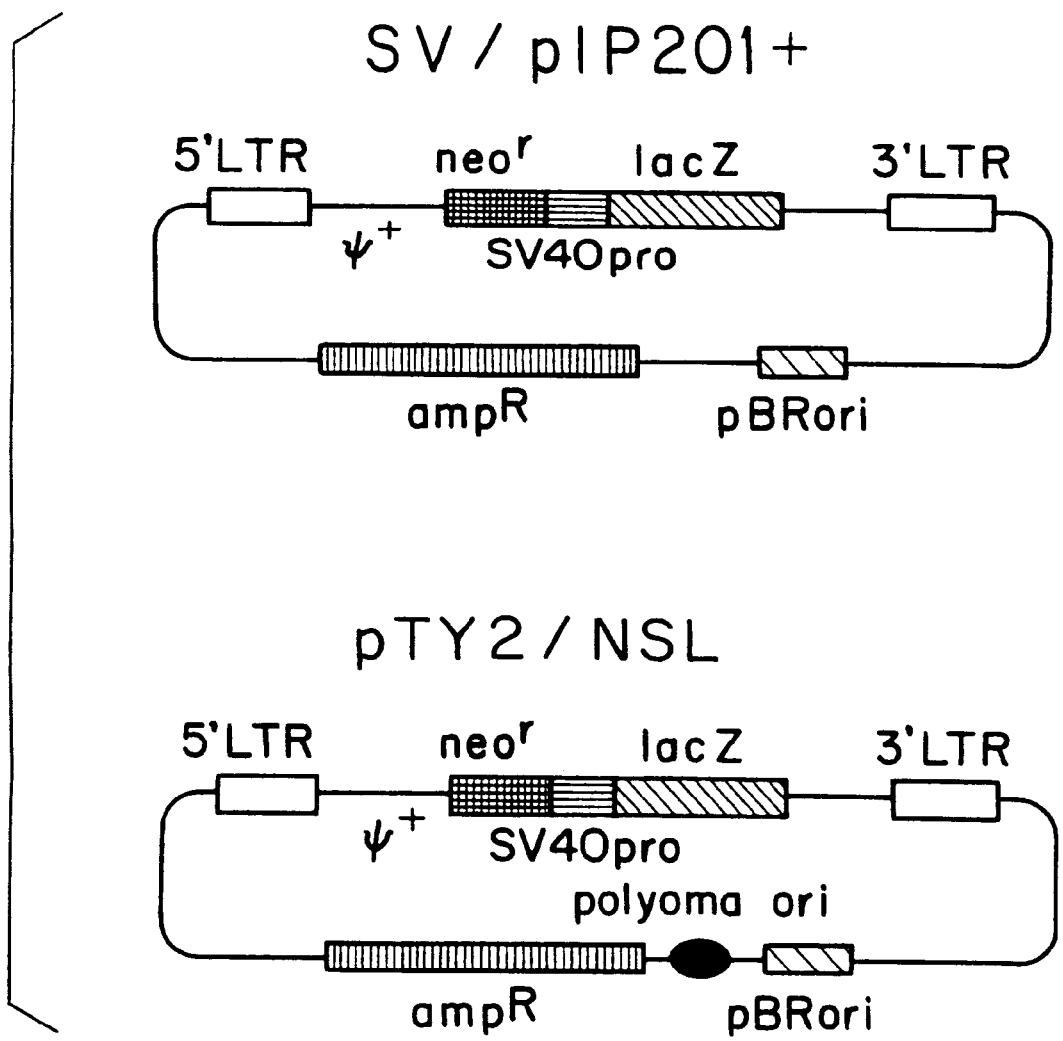
F I G. 2

CELLS PRODUCING RECOMBINANT RETROVIRUS

This application is a national stage application of international application PCT/JP96/01484, filed May 31, 1996.

FIELD OF THE INVENTION

The present invention relates to cells producing a recombinant retrovirus.

BACKGROUND ART

A method for introducing a retrovirus as a vector into higher animal cells has excellent features such as less cytotoxicity associated with gene transfer and integration of the transferred gene into the chromosome with stable maintenance. For these reasons, this method has not only been used for experimental gene transfer but for gene therapy as well. The retrovirus used as a vector is mainly derived from the Moloney Murine Leukemia Virus (MoMuLV), but a retrovirus derived from the Avian Leukosis Virus (ALV) has also been developed. These retroviruses have a single-strand RNA as a genome, on which gag, pol and env genes coding for proteins necessary for virus construction are located. The viral RNA genome is coated by capsid proteins and further coated by matrix proteins, transmembrane proteins and surface proteins. These viral coating proteins are encoded by the gag and env genes. Further, the pol gene codes for reverse transcriptase, protease and integrase which are important in the viral life cycle.

When cells are infected with such a retrovirus, the viral RNA is transcribed into DNA by reverse transcriptase, and the resultant DNA is integrated into a cellular chromosome by integrase to make a provirus. The gag, pol and env genes are expressed by this provirus to construct a viral particle and an RNA viral genome is produced at the same time. This viral RNA is then encapsidated into the viral particle to replicate the virus. When produced from the cell, this virus can infect other cells.

In order to use this retrovirus as a vector, it is necessary to prepare a "recombinant retrovirus" into which a foreign gene has been introduced. A fundamental method for preparing a recombinant retrovirus has been established, in which the recombinant retrovirus is prepared using a particular cell called a "packaging cell".

In a packaging cell, a retrovirus genome having the gag, pol and env genes is integrated into a chromosome, and all the proteins necessary to construct a viral particle are expressed by the integrated genes. A mutation has been introduced in said retrovirus-derived genome. Namely, the ψ region, which is necessary to encapsidate the virus genome into the viral particle, is deleted, and thus the RNA genome cannot be encapsidated into the viral particle. When a plasmid which have the ψ region, two long terminal repeat regions (LTRs) (generally, they are 5' LTR and 3' LTR, where the initiation region of reverse transcription and promoter and enhancer sequences are located in 5' LTR, and a poly A addition signal is located in 3' LTR), and the foreign gene franked between two LTRs, are introduced into a packaging cell line, the RNA genome derived from this plasmid is encapsidated into the viral particle. A retrovirus vector having a foreign gene is thus produced. This recombinant retrovirus infects a target cell and integrates the foreign gene into the chromosome of the infected cell, wherein said foreign gene can stably be expressed in the target cell.

In introducing a gene into a packaging cell, the greater the production of retrovirus by the cell, that is, the higher the viral titer, the greater the number of cells into which said gene is introduced. Introduction of a gene into a large number of cells facilitates experiments for gene transfer and is important for efficient gene therapy.

In order to increase the viral titer, recombinant plasmids DOL and DOL$^-$ have been constructed, which have the Polyoma virus early region gene and the replication origin containing the promoter of this early region gene (A. J. Korman, J. D. Frantz, J. L. Strominger and R. C. Mulligan: Expression of human class II major histocompatibility complex antigens using retrovirus vectors. Proc. Natl. Acad. Sci. USA, 84, 2150–2154 (1987)). These recombinant plasmids are a case to which the Polyoma virus early region gene and its replication system are applied.

The polyoma virus is a circular DNA virus infectious to rodents. When this virus infect to a cell, the early region gene which consists of the large T antigen, middle T antigen and small T antigen is expressed, and the large T antigen protein acts on the replication origin of the viral DNA to start replication. At this time, the viral DNA molecule is multiplied in the nucleus of the infected cell and multicopy production is observed. Such multicopies are considered to be valuable if they have the early region gene and the origin of replication containing the promoter region of the early region gene. Since the recombinant plasmids DOL and DOL– have the polyoma early region containing the polyoma replication origin, they exist as multicopies in the packaging cells, which is deemed to be responsible for the increased production of recombinant retrovirus derived from the plasmids.

Such a polyoma virus replication system has also been applied to expression of a foreign gene using cell culture systems. Known examples include MOP cells and WOP cells, in which the Polyoma virus early region gene has first been introduced into the culture cells. When a plasmid having the Polyoma virus replication origin is introduced in MOP cells or WOP cells, the large T antigen protein expressed by the early region gene causes an increase in the number of copies of the introduced plasmid (for example, 500 to 2,000 copies). As a result, the level of expression of a foreign gene inserted into the plasmid increases.

A plasmid introduced into a cell is exist either as an extrachromosomal DNA or in the form of DNA integrated into the chromosome. When the plasmid is exist as an extrachromosomal DNA, the number of copies of plasmid increases due to the action of the Polyoma virus large T antigen protein; however, the increase is transient and the number of copies reaches a peak 48 to 72 hours after plasmid introduction or expression of the large T antigen protein, and then decrease. Also, when the plasmid is integrated into the chromosome, the introduced gene is excised from the chromosome and is lost from the cells due to the action of the Polyoma virus replication origin and the large T antigen protein of Polyoma virus. It has been reported from these results that the massive expression of foreign genes is not a stable but a temporary phenomenon (F. G. Kern and C. Basilico: An inducible eukaryotic host-vector expression system: Amplification of genes under the control of the Polyoma late promoter in a cell line producing a thermolabile large T antigen. Gene 43, 237–245 (1986)).

A cell line Wgd5, in which the Polyoma virus early region is integrated, has been developed as a packaging cell (A. J. M. Murphy and A. Efstratiadis: Cloning vectors for expression of cDNA libraries in mammalian cells. Proc. Natl. Acad. Sci. USA. 84, 8277–8281 (1987)). Wgd5 cell is a packaging cell which is constructed by introducing the Mo-MuLV genome with a deleted ψ region into its parent strain, namely WOP cell (NIH 3T3 cell transformed by the Polyoma virus genome in which the promoter and the origin of replication are inactivated). When a recombinant plasmid having the origin of replication derived from Polyoma virus is introduced into this Wgd5 cell, the level of replication increases, though transiently. If this recombinant plasmid contains the LTR of Mo-MuLV and the ψ region, the recombinant retrovirus is produced.

SUMMARY OF THE INVENTION

The present inventors have found that a higher viral titer can be attained in a packaging cell in which the Polyoma virus early region gene is introduced. The present invention is based on such a finding.

Accordingly, an objective of the present invention is to provide a cell producing a recombinant retrovirus for preparing a virus having a higher viral titer.

Further, the cell producing a recombinant retrovirus of the present invention are constructed by introducing the Polyoma virus early region gene together with a recombinant plasmid or a recombinant retrovirus free from any replication origin derived from the Polyoma virus into a packaging cell for preparing a recombinant retrovirus.

BRIEF DESCRIPTION OF THE DRAWINGS

FIG. 2 shows the structure of a recombinant plasmid which stably produces a recombinant retrovirus when introduced into a packaging cell.

DETAILED DESCRIPTION OF THE INVENTION

Figure 1:
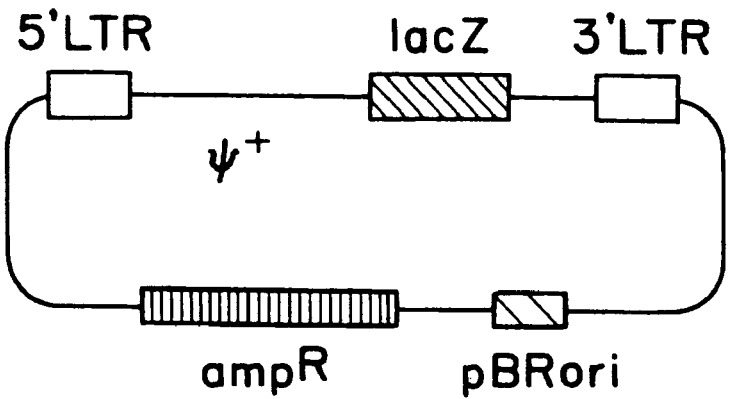
FIG. 1 shows the structure of a recombinant plasmid which transiently produces a recombinant retrovirus when introduced into a packaging cell.
Figure 1:
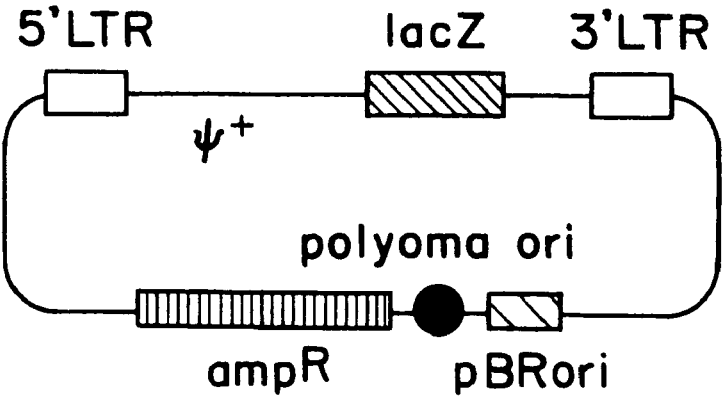

The term "packaging cell" as used herein denotes a cell in which a viral genome with a deleted ψ region, which is necessary for encapsidate into a viral particle, is introduced and all the proteins, which are necessary for construction of viral particles, are expressed. The term "packaging cell" as used herein, without further explanation, denotes a cell in which no recombinant plasmid or recombinant plasmid for production of a recombinant retrovirus is introduced.

The term "recombinant plasmid" as used herein denotes a plasmid which is introduced into the packaging cell for preparation of a recombinant retrovirus.

Further, the term "cell producing a recombinant retrovirus" denotes a cell for preparation of a recombinant retrovirus which is obtained by introduction of the "recombinant plasmid" or "recombinant retrovirus" into the "packaging cell".

The cell producing a recombinant retrovirus of the present invention is a packaging cell in which the Polyoma virus early region gene is introduced, and the recombinant retrovirus or recombinant plasmid which is introduced into the packaging cell does not contain any replication origin derived from Polyoma virus.

Conventionally, the Polyoma virus early region gene has been used in combination with a plasmid having the Polyoma virus replication origin to produce retroviruses or substances. As mentioned above, it was difficult to sustain stable retrovirus production since the retrovirus was transiently produced with a subsequent decrease in the number of copies and a loss of the introduced gene.

In view of such prior art, it is surprising that a recombinant retrovirus having a higher viral titer can be stably produced by introducing a retrovirus plasmid or recombinant retrovirus into packaging cells in which the Polyoma virus early region gene is introduced.

According to a preferred embodiment of the present invention, stable production of recombinant retrovirus in the cells of the present invention is about 6 times greater than in a system using packaging cells free from the Polyoma early region gene. Furthermore, according to a preferred embodiment of the present invention, transient production of a recombinant retrovirus in the cells of the present invention is about 50 to 100 times greater than in a system using packaging cells free from the Polyoma early region gene.

Further, the cells producing a recombinant retrovirus of the present invention are different from the recombinant retrovirus production system in which DOL or DOL⁻ is introduced in that the Polyoma virus is introduced in packaging cells without being linked to a recombinant plasmid or recombinant retrovirus having a foreign gene (namely, the Polyoma virus early region gene is introduced into packaging cells independently from a retrovirus plasmid or a recombinant retrovirus).

The Polyoma virus early region gene used in the present invention is present in the Polyoma virus genome and can be obtained, for example, from plasmid pPyBamHI (VG020 obtained from the Gene Bank of National Institute of Health in Japan; available at the Human Science Research Resource Bank after Oct. 1, 1995) or Polyoma strain A2 (ATCC45017).

In the present invention, packaging cells, except those in which the Polyoma virus early region gene is introduced, may be packaging cells commonly used. Examples of such packaging cells include ψ2 cell, ψ-AM cell, PA12 cell, PA317 cell, ψCRE cell, ψCRIP cell, GP+envAM12 cell, GP+E-86 cell, ΩE cell and ampli-GPE cell.

Introduction of the Polyoma virus early region gene into packaging cells can be performed by a usual method, including the calcium phosphate method, the use of a commercial transfection kit, the electroporation method and the DEAE-dextran method.

The Polyoma virus early region gene introduced into packaging cells is preferably operably linked to the promoter. Examples of preferable promoters include promoters generally used in animal cells. Examples of such promoters include the metallothionein promoter, the cytomegalovirus immediate early (IE) gene promoter, the SV40 virus early region gene promoter (SV40 pro), LTR promoters of MMLV, MMSV, RSV and MMTV, and modified promoters thereof. Preferable promoters are the metallothionein promoter and the cytomegalovirus IE gene promoter.

In the cells producing a recombinant retrovirus according to the present invention, a recombinant retrovirus having a foreign gene is produced by introducing a recombinant plasmid or a recombinant retrovirus having the foreign gene into packaging cells. Specifically, the recombinant plasmid or the recombinant retrovirus comprises two LTR (i.e., 5' LTR and 3' LTR), a foreign gene, and the ψ region but is free from any replication origin derived from Polyoma virus. The foreign gene in the recombinant plasmid or recombinant retrovirus is located at a site downstream from 5' LTR and upstream from 3' LTR. The recombinant retrovirus can be obtained, for example, by introducing the recombinant plasmid into packaging cells. These packaging cells may or may not contain the Polyoma virus early region gene.

The type of the foreign gene is not particularly restricted and the size of the gene is also appropriately selected depending on a vector to be used. Further, the foreign gene can operably be linked to an optional promoter other than 5' LTR promoter (e.g., a promoter derived from SV40). The recombinant plasmid according to the present invention does not contain a 3.6 kb fragment of the Polyoma virus early region gene as does the plasmid DOL or DOL− which has the conventional Polyoma virus early region gene. Accordingly, this recombinant plasmid is also very useful in easing the size restriction of the foreign gene to be inserted into the recombinant site. According to a preferred embodiment, for example, a foreign gene which has a size of up to about 8 kbp can be introduced when pTY1 is used as a plasmid.

Transfection of a recombinant plasmid into packaging cells can be performed by a conventional method. For example, the calcium phosphate method, the electroporation method, the DEAE-dextran method and the lipofection method are available. A commercial transfection kit are also available. Introduction of a recombinant retrovirus into packaging cells can also be performed by a conventional method.

When a recombinant plasmid or a recombinant retrovirus is introduced, a selectable marker gene to select infected (or transfected) cells can be included within the recombinant plasmid or the recombinant retrovirus. When a recombinant plasmid having no selectable markers is introduced, cotransfection with another plasmid having a selectable marker can be performed. Examples of the selectable marker include the neomycin resistant gene, the hygromycin resistant gene, and the blasticidin resistant gene. When a recombinant retrovirus having no selectable markers is introduced, infected cells can be selected using instruments to identify and isolate the infected cells.

Further, in the present invention, a vector having the Polyoma virus early region gene and a recombinant plasmid can be introduced into packaging cells by a cotransfection method. The packaging cells in which a recombinant plasmid thus is introduced also produce a recombinant retrovirus having a higher viral titer.

Culture conditions for packaging cells can be appropriately selected for individual cells. According to a preferred embodiment of the present invention, when the metallothionein promoter is used, a higher viral titer can be attained even when the promoter is not under conditions necessary to induce expression by this promoter (i.e., in the presence of metal ions). Therefore, the culture condition is not limited to the presence of metal ions.

EXAMPLES

The present invention will be explained in more detail by the following Examples. However, the invention is not intended to be limited to the Examples.

Example 1
Preparation of Packaging Cells in which the Polyoma Virus Early Region Gene is Introduced
(1) Construction of vector for expression of Polyoma virus early region gene The Polyoma virus early region gene used is the fragment between EarI site (nucleotide No. 140; HpaII site within the replication origin is referred to as nucleotide No. 1) and HincII site (nucleotide No. 2962) of plasmid pPyBamHI (VG020) (obtained from the Gene Bank of National Institute of Health in Japan; available at the Human Science Research Resource Bank after Oct. 1, 1995) in which Polyoma virus is cloned.

An expression vector for the Polyoma virus early region gene was constructed as follows: First, the coding region was separated from the promoter and the replication origin and then subcloned. For this, the EarI site at about 40 bp upstream of the starting codon of the Polyoma virus early region was used.

Another EarI site is present also in the coding region of the Polyoma virus early region. Accordingly, the EcoRI site existing separately in the coding region was used to divide the plasmid into two fragments. First, the plasmid having the Polyoma virus genome was cut with EarI and the resulting fragment was blunted with DNA polymerase Klenow fragment and a HindIII linker was ligated into the blunt end. In this manner, the 5' side of the coding region was prepared as a HindIII-EcoRI fragment. To prepare the 3' side of the coding region, the plasmid was cut at the HincII site located at about 50 bp downstream of the stop codon and a XhoI linker was ligated into the site. In this manner, the 3' side of the coding region was prepared as an XhoI-EcoRI fragment. These two fragments were ligated into the XhoI-HindIII site of the cloning vector pBluescript II (pB/polyoma).

Next, in order to express the Polyoma virus early region thus constructed in the cells, the resulting fragment was ligated with the metallothionein promoter. The BamHI-XhoI fragment containing the Polyoma virus early region was inserted into the BamHI-XhoI site of a plasmid having the metallothionein promoter (pMTX). This construct is hereinafter referred to as "pMTX/polyoma". A poly A addition signal is contained in the region derived from the Polyoma virus.

(2) Introduction of Polyoma virus early region gene into packaging cells

Introduction of pMTX/polyoma into packaging cells was carried out as follows: As the pMTX/polyoma has no selectable markers which function in cultured cells, it was cotransfected with another plasmid bearing a selectable marker and then introduced into the cells. Namely, 2 µg of the plasmid and 0.2 µg of pSV2bsr bearing the blasticidin resistant gene (Funakoshi) were mixed and introduced into packaging cells, ψ2, PA317 or ψCRIP, using the lipofectoamine reagent to select strains which showed blasticidin resistance.

The PCR method was used to select clones in which the Polyoma virus early region gene derived from the blasticidin resistant strain was introduced. Blasticidin resistant strains, i.e., 35 strains derived from ψ2, 49 strains derived from PA317 and 29 strains derived from ψCRIP, were cultured on 3.5-cm diameter dishes, grown cells were treated with trypsin (0.025%/PBS) to strip them from the dishes, then centrifuged for recovery. The recovered cells were suspended in 30 µl of TE buffer, 300 µl of an extracting buffer (10 mM Tris-HCl (pH 8.0), 0.1 M EDTA (pH 8.0), 0.20 µg/ml RNase, 0.5% SDS) were added, and incubation was carried out at 37° C. for 1 hour. Then, proteinase K was added to make a final concentration of 100 µg/ml and incubation was carried out at 50° C. overnight. Extraction was carried out once with an equal volume of phenol, then again with phenol/chloroform. Ammonium acetate was added to make a final concentration of 2 M, and then 2 volumes of ethanol were added. String-like DNA formed after mixing was hooked onto the tip of a Pipetman and transferred into a 70% aqueous ethanol solution. DNA was recovered by centrifugation, dried in air, then dissolved in 100 µl of TE buffer. Concentration of DNA was measured by optical density (OD at 260 nm), then the solutions were adjust to 1 µg/10 µl. Individual DNA solutions were subjected to the PCR method to select 2 strains each of clones, in which the Polyoma virus early region gene was introduced, from each packaging cell, i.e., ψMP34 and ψMP37 from ψ2, PAMP41 and PAMP51 from PA317, and CRIPMP2 and CRIPM20 from ψCRIP.

Example 2

Titer of Recombinant Retrovirus Transiently Produced from Packaging Cells in which the Polyoma Virus Early Region Gene was Introduced (1) Structure of recombinant plasmid to be introduced into packaging cells and construction thereof Two different kinds of recombinant plasmids were used in this Example (see FIG. 1).

pTY1/lacZ is a recombinant plasmid having 5' LTR, 3' LTR and the ψ region and the lacZ gene as a reporter gene and free from any replication origin derived from Polyoma virus. This recombinant plasmid was constructed as follows: pIF9171 (K. Ikenaka et al.: Detection of Brain-specific Gene Expression in Brain Cells in Primary Culture: A Novel Promoter Assay Based on the Use of a Retrovirus Vector. The New Biologist 4, 53–60 (1992)) was cut with the restriction enzymes AatII and NcoI, and a fragment which was excised from pLN (A. D. Miller and G. J. Rosman: Improved Retroviral Vectors for Gene Transfer and Expression. BioTechniques 7, 980–990 (1989)) with AatII and NcoI was inserted into the resulting site to construct pSI9171+. The pSI9171+ was cut with the restriction enzyme EcoRI and was re-ligated to construct pTY1. The pTY1 was cut with the restriction enzyme HindIII and the lacZ gene excised with HindIII from SPUD, which was provided by Dr. C. L. Cepko of Harvard Medical School (C. Walsh & C. L. Cepko: Clonally Related Cortical Cells Show Several Migration Patterns. Science 241, 1341–1345 (1988)), was inserted into the resulting site to construct pTY1/lacZ.

pTY2/lacZ has the same structure as pTY1/lacZ except that it has the Polyoma virus replication origin. pTY2/lacZ was constructed as follows: pPyBamHI (GV020) was cut at HinfI sites (nucleotide Nos. 5093 and 385) to prepare Polyoma virus replication origin as a fragment of about 0.6 kpb. This fragment was treated with DNA polymerase Klenow fragment to make a blunt end, into which the NotI linker (Takara Shuzo) was ligated. The fragment thus obtained was cut with NotI and the resulting fragment was inserted at the NotI site of pTY1/lacZ to construct pTY2/lacZ.

(2) Titer of recombinant retrovirus transiently produced from packaging cells

The packaging cells ψMP34, ψMP37, PAMP41, PAMP51, CRIPMP2 and CRIPM20 were inoculated on dishes (3.5 cm in diameter) at a concentration of $1-2 \times 10^5$/dish, and 2 μg of pTY1/lacZ or pTY2/lacZ were transfected using the lipofectamine reagent (GIBCO BRL) on the following day. The same plasmid was introduced into parent strains of the packaging cells, i.e., ψ2, PA317 and ψCRIP, for comparison. Further, in all combinations of the experiments using ψMP34, ψMP37 and ψ2, culture was carried out in the presence and absence of $ZnCl_2$ (100 μM) to examine the difference with and without induction by the metallothionein promoter. After culturing for 2 days, the culture supernatant was recovered to obtain a recombinant retrovirus fraction. NIH3T3 cells, which had been cultured on dishes (3.5 cm in diameter) at a concentration of $1 \times 10^5$/dish overnight, were infected with 1–10 μl of this virus fraction and incubation was carried out for 2 days. Virus-infected cells were detected by the X-gal staining and the viral titer for the recombinant retrovirus was obtained. Results are shown in Table 1.

TABLE 1

Viral titer of transiently produced recombinant retrovirus

| Packaging cell | Viral titer ($\times 10^3$ cfu/ml) | | | |
|---|---|---|---|---|
| | pTY1/lacZ | | pTY2/lacZ | |
| | -Zn | +Zn | -Zn | +Zn |
| Ψ2 | 9.6 ± 1.7 | 10.2 ± 0.8 | 20.6 ± 1.7 | 14.2 ± 2.9 |
| ΨMP34 | 410.6 ± 22.6 | 429.7 ± 47.8 | 516.3 ± 44.9 | 655.1 ± 150.8 |
| ΨMP37 | 989.7 ± 133.7 | 1007.7 ± 39.3 | 1491.0 ± 188.5 | 1535.0 ± 294.6 |
| PA317 | 15.2 ± 1.2 | | 18.4 ± 1.1 | |
| PAMP41 | 148.4 ± 6.9 | | 237.9 ± 0.8 | |
| PAMP51 | 194.7 ± 7.4 | | 289.0 ± 7.5 | |
| ΨCRIP | 5.3 ± 1.2 | | 4.8 ± 0.5 | |
| CRIPM2 | 119.5 ± 12.7 | | 173.0 ± 13.5 | |
| CRIPM20 | 144.8 ± 11.2 | | 156.4 ± 10.4 | |

Recombinant retroviruses transiently produced from ψMP34 and ψMP37 showed viral titers 50–100 times higher than those transiently produced from their parent strain ψ2 regardless of the presence or absence of Polyoma viral replication origin in the recombinant retrovirus. Recombinant retroviruses produced transiently from PAMP41 and PAMP51 showed viral titers 9–16 times higher than those produced from their parent strain PA317. Recombinant retroviruses produced transiently from CRIPMP2 and CRIPMP20 showed viral titers 22–36 times higher than those produced from their parent strain ψCRIP. Accordingly, this recombinant retrovirus production system, in which a recombinant plasmid free from any replication origin of Polyoma virus is introduced into packaging cells in which the Polyoma virus early region gene is introduced, is far superior to the conventional recombinant retrovirus production system (namely, the system in which a recombinant plasmid is introduced in the parent strain ψ2, PA317 and ψCRIP). However, as to the titer of recombinant retroviruses produced from packaging cells in which the Polyoma virus early region gene was introduced (i.e., ψMP34, ψMP37, PAMP41, PAMP51, CRIPMP2 and CRIPMP20), the cells with recombinant plasmid pTY2/lacZ having the Polyoma virus replication origin showed viral titers about 1.5 times higher than those with pTY1/lacZ free from any Polyoma virus replication origin. Thus, the combination of the Polyoma virus early region gene and the replication origin was advantageous in the transient production of recombinant retrovirus.

Example 3

Titer of Recombinant Retrovirus Stably Produced from Packaging Cells in which the Polyoma Virus Early Region Gene was Introduced (1) Structure of recombinant plasmid to be introduced into packaging cells and its construction Two kinds of recombinant plasmids were used in this Example (see FIG. 2).

SV/pIP201+ has the neomycin resistant gene as a selectable marker and lacZ linked to SV40 promoter as a reporter gene and free from any replication origin derived from Polyoma virus. SV/pIP201+ was constructed as follows: pIP200 (K. Ikenaka et al.: Detection of Brain-specific Gene Expression in Brain Cells in Primary Culture: A Novel Promoter Assay Based on the Use of a Retrovirus Vector. The New Biologist 4, 53–60 (1992)) was cut with restriction enzyme SalI-HindIII, and the SV40 promoter excised from SPUD with a SalI-HindIII fragment was inserted into the resulting site to construct SV/pIP201. The SV/pIP201 was cut with EcoRI to prepare a fragment containing the neomycin resistant gene, the SV40 promoter and a part of the lacZ gene. This fragment was inserted into the EcoRI site of pTY1/lacZ to construct SV/pIP201+.

pTY2/NSL has the neomycin resistant gene as a selectable marker, lacZ ligated with the SV 40 promoter as a reporter and the replication origin derived from Polyoma. PTY2/NSL was constructed by inserting the fragment obtained by cutting SV/pIP201 with EcoRI at the EcoRI site of pTY2/lacZ.

(2) Titer of recombinant retrovirus stably produced from packaging cells (1)

SV/pIP201+ or pTY2/NSL was introduced into the packaging cell ψMP34 and parent cell ψ2 using the Lipofectoamine Reagent. Clones which became resistant to the drug G418 by the action of the neomycin resistant gene on the introduced plasmid were selected.

Cells of 10 clones thus obtained were cultured in the following method to prepare recombinant retroviruses and their titers were examined. Cells of each clone were inoculated on 3 dishes (3.5 cm in diameter) at a concentration of $5 \times 10^4$/dish. After culturing for 3 days, when the culture became subconfluent, the culture volume was reduced by half and the dishes were transferred to an incubator set at 32° C. After culturing for 2 days, the culture supernatant was recovered and NIH3T3 cells were infected with 1 μl or 10 μl of this virus fraction. Incubation was carried out for 2 days, the X-gal staining was carried out, and then the viral titer for the recombinant retrovirus was obtained. Results for clones showing the highest titers are shown in Table 2.

TABLE 2

Viral titer of stably produced recombinant retrovirus (1)

| Packaging cell | Plasmid # | Viral titer ($\times 10^5$ cfu/ml) |
|---|---|---|
| ΨMP34 | SV/pIP201 + 4 | 288.54 ± 12.83 |
|  | pTY2/NSL 7 | 152.3 ± 8.19 |
| Ψ2 | SV/pIP201 + 7 | 50.37 ± 4.81 |
|  | pTY2/NSL 8 | 19.75 ± 3.33 |

The recombinant retrovirus produced from clone #4 which was obtained by introducing recombinant plasmid SV/pIP201+ free from any replication origin of Polyoma virus into ψMP34 showed a viral titer (about $2.9 \times 10^7$ cfu/ml) about 2 times higher than that of recombinant retrovirus produced from clone #7 which was obtained by introducing recombinant plasmid pTY2/NSL having the replication origin of Polyoma virus into the same packaging cells (i.e., about $1.5 \times 10^7$ cfu/ml). This result suggests that introduction of the Polyoma virus replication origin is not necessary to obtain a clone which can stably produce a recombinant retrovirus which shows a higher viral titer.

The recombinant retrovirus produced from clone #4 which was obtained by introducing SV/pIP201+ into ψMP34 showed a viral titer about 6 times higher than that produced by clone #7 which was obtained by introducing SV/pIP201+ into the parent strain ψ2 ($5.0 \times 10^6$ cfu/ml).

(3) Titer of recombinant retrovirus stably produced from packaging cells (2)

SV/pIP201+ was introduced into packaging cell PA317 using the Lipofectoamine Reagent and after incubation for 2 days, a fraction of transiently produced recombinant retrovirus was prepared. Packaging cells ψMP34 and ψMP37 and their parent strain ψ2 were infected with the resulting recombinant retrovirus. Cells infected with the recombinant retrovirus were selected using the drug G418. The polyoma virus replication origin is not included in the expression unit thus introduced into the packaging cells. The resulting clones were cultured in the same manner as in (2) above and titers of retroviruses produced were examined. Results obtained from randomly selected 11 clones are shown in Table 3.

TABLE 3

Viral titer of stably produced recombinant retrovirus (2)

| | Viral titer ($\times 10^5$ cfu/ml) | | |
|---|---|---|---|
| Clone # | Ψ2 | ΨMP34 | ΨMP37 |
| 1 | 65.1 | 161.5* | 187* |
| 2 | 65.8 | 83.2 | 119.7* |
| 3 | 70.9 | 14.4 | 30.8 |
| 4 | 103.7* | 16.8 | 86.5 |
| 5 | 5.7 | 126.9* | 145.7* |
| 6 | 1.2 | 131.3* | 259.6* |
| 7 | 105.2* | 198.1* | 112.5* |
| 8 | 62.0 | 413.5* | 121.2* |
| 9 | 36.5 | 127.4* | 61.1 |
| 10 | 28.5 | 41.0 | 189.4* |
| 11 | 16.3 | 285.1* | 237.0* |

When the parent strain ψ2 was infected with a retrovirus, recombinant retroviruses having a titer over $1 \times 10^7$ cfu/ml were produced in 2 out of 11 clones (#4 and #7 indicated with *). On the other hand, recombinant retroviruses having a titer over $1 \times 10^7$ cfu/ml were produced in 7 out of 11 clones when ψMP34 was infected, and 8 out of 11 clones when ψMP37 was infected (clones with *). The packaging cells in which the Polyoma virus early region gene was introduced (ψMP34, #8) showed a titer of $4.14 \times 10^7$ cfu/ml about 4 times higher than the maximum titer shown in ψ2 (i.e., $1.05 \times 10^7$ cfu/ml). In this way, ψMP34 or ψMP37 enabled to produce packaging cells producing a recombinant retrovirus having a higher viral titer than that obtainable by parent strains.

(4) Titer of recombinant retrovirus stably produced from packaging cells (3) SV/pIP201+ was introduced into packaging cell ψ2 using the lipofecctoamine Reagent and after incubation for 2 days, a fraction of transiently produced recombinant retrovirus was prepared. Packaging cell PAMP51 or its parent strain PA317 was infected with the resulting recombinant retrovirus. Cells infected with the recombinant retrovirus were selected using the drug G418. The Polyoma virus replication origin is not included in the expression unit thus introduced into the packaging cells. The resulting clones were cultured in the same manner as in (2) above and titers of retroviruses produced were examined. Results obtained from randomly selected 10 clones are shown in Table 4.

TABLE 4

Viral titer of stably produced recombinant retrovirus (3)

| | Viral titer ($\times 10^5$ cfu/ml) | |
|---|---|---|
| Clone # | PA317 | PAMP51 |
| 1 | 55.5 | 781 |
| 2 | 5.3 | 117.5 |

TABLE 4-continued

Viral titer of stably produced recombinant retrovirus (3)

| Clone # | Viral titer (× 10⁵ cfu/ml) | |
| --- | --- | --- |
|  | PA317 | PAMP51 |
| 3 | 6.5 | 66.7 |
| 4 | 16.4 | 118.5* |
| 5 | 8.5 | 83.7 |
| 6 | 6.6 | 99.0 |
| 7 | 16.5 | 53.9 |
| 8 | 9.5 | 65.0 |
| 9 | 17.7 | 16.2 |
| 10 | 39.2 | 90.2 |

When the parent strain PA317 was infected with a recombinant retrovirus, no clone produced recombinant retroviruses having a titer over $1\times10^7$ cfu/ml. On the other hand, recombinant retroviruses having a titer over $1\times10^7$ cfu/ml were produced in 2 out of 10 clones when PAMP51 was infected (clones with *). The maximum titer shown in PAMP51 was $1.18\times10^7$ cfu/ml, about 3 times higher than that shown in PA317 ($0.39\times10^7$ cfu/ml). Thus, PAMP51 facilitates the production of packaging cells producing a recombinant retrovirus having a higher viral titer than that obtainable by its parent strain.

Example 4
Experiments Regarding Promoter to Express Polyoma Virus Early Region
(1) Structure of recombinant plasmid and Polyoma virus early region expression vector used in this Example and their constructions pTY1/lacZ and pTY2/lacZ were used as recombinant plasmids in this Example. pB/CMV-polyoma linked to the human cytomegalovirus IE gene promoter was used as the Polyoma virus early region. This pB/CMV-polyoma was constructed by inserting the cytomegalovirus promoter obtained by cutting pLNCX (A. D. Miller and G. J. Rosman: Improved Retroviral Vectors for Gene Transfer and Expression. BioTechniques 7, 980–990 (1989)) with BamHI and HpaI at the BamHI-SmaI site of pB/polyoma. Further, pB/polyoma was also used as a control.

(2) Introduction of recombinant plasmid and polyoma virus early region expression vector by cotransfection method into packaging cells and titer of transiently produced recombinant retrovirus The recombinant plasmid (pTY1/lacZ or pTY2/lacZ) together with pB/CMV-polyoma or pB/polyoma was introduced into packaging cell ψ2 and titers of transiently produced recombinant retroviruses were examined. Packaging cell ψ2 was inoculated on dishes (3.5 cm in diameter) at a concentration of $1\times10^5$/dish, and recombinant plasmids and vectors were introduced using the Lipofectamine Reagent on the following day in the following combinations: 1) pTY1/lacZ and pB/polyoma, 2) pTY1/lacZ and pB/CMV-polyoma, 3) pTY2/lacZ and pB/polyoma, and 4) pTY2/lacZ and pB/CMV-polyoma. 1 μg each of plasmids was used. After culturing for 2 days for the transient production of recombinant retroviruses, the culture supernatant was recovered to obtain a recombinant retrovirus fraction. NIH3T3 cells, which had been cultured on dishes (3.5 cm in diameter) at a concentration of $1\times10^5$/dish overnight, was infected with 10 μl of this virus fraction and incubation was carried out for 2 days. Virus-infected cells were detected by the X-gal staining and the viral titer for the recombinant retrovirus was obtained. Results are shown in Table 5.

TABLE 5

Viral titer of recombinent retrovirus transiently produced by cotransfection of CMV-polyoma and recombinant plasmid

| # | Viral titer (× 10³ cfu/ml) |
| --- | --- |
| 1) pTY1/lacZ + pB/polyoma | 7.66 ± 1.37 |
| 2) pTY1/lacZ + pB/CMV-polyoma | 26.23 ± 4.14 |
| 3) pTY2/lacZ + pB/polyoma | 13.69 ± 1.42 |
| 4) pTY2/lacZ + pB/CMV-polyoma | 84.70 ± 16.53 |

Recombinant retroviruses produced by introducing the recombinant plasmid together with the Polyoma virus early region expression vector using the constitutively expressing cytomegalovirus promoter into the packaging cells yielded a higher viral titer than recombinant retroviruses produced using the Polyoma virus early region gene expression vector in which the early region gene was not ligated with a promoter. The viral titer increased by about 6.2-fold by the introduction of the Polyoma virus replication origin was in the case of pTY2/lacZ and about 3.4-fold even without the introduction of said replication origin. In other words, recombinant retrovirus production was significantly increased by linking a promoter to the Polyoma virus early region gene, for which the cytomegalovirus early region gene promoter and the metallothionein promoter were proven to be effective.

We claim:

1. A cell line which produces a recombinant retrovirus, wherein said cell line is obtained by introducing into a packaging cell:
   (A) a vector comprising the Polyoma virus early region gene operably linked to a promoter, and
   (B) a recombinant plasmid or a recombinant retrovirus comprising 5' LTR, 3' LTR, and the ψ region, wherein the recombinant plasmid or the recombinant retrovirus is free from any replication origin obtained from Polyoma virus.

2. The cell line of claim 1, wherein said recombinant plasmid or recombinant retrovirus further comprises a foreign gene.

3. The cell line of claim 1, wherein said promoter is the metallothionein promoter or the cytomegalovirus IE gene promoter.

4. The cell line of claim 1, wherein the Polyoma virus early region is obtained from Polyoma strain A2.

5. The cell line of claim 1, wherein the packaging cell is selected from the group consisting of ψ2 cells, ψ-AM cells, PA12 cells, PA317 cells, ψCRE cells, ψCRIPcells, GP+envAM12 cells, GP+E-86 cells, ΩE cells and ampli-GPE cells.

6. The cell line of claim 1, wherein the foreign gene is operably linked to a promoter.

7. A method for producing a recombinant retrovirus, comprising culturing the cell line of claim 1 for a time sufficient to produce the recombinant retrovirus.

8. A method of producing the cell of claim 1, comprising:
   introducing into a packaging cell:
   (A) a vector comprising the Polyoma virus early region gene operably linked to a promoter, and
   (B) a recombinant plasmid or a recombinant retrovirus comprising 5' LTR, 3' LTR, and the ψ region, wherein the recombinant plasmid or the recombinant retrovirus is free from any replication origin obtained from Polyoma virus.

9. The method of claim 8, wherein (A) and (B) are cotransfected into the packaging cell.

10. The method of claim 8, wherein said recombinant plasmid or recombinant retrovirus further comprises a foreign gene.

11. The method of claim 8, wherein said promoter is the metallothionein promoter or the cytomegalovirus IE gene promoter.

12. The method of claim 8, wherein the Polyoma virus early region is obtained from Polyoma strain A2.

13. The method of claim 8, wherein the packaging cell is selected from the group consisting of ψ2 cells, ψ-AM cells, PA12 cells, PA317 cells, ψCRE cells, ψCRIPcells, GP+envAM12 cells, GP+E-86 cells, ΩE cells and ampli-GPE cells.

14. The method of claim 8, wherein the foreign gene is operably linked to a promoter.

\* \* \* \* \*